(12) United States Patent
Shatkin (10) Patent No.: US 10,631,959 B2
(45) Date of Patent: Apr. 28, 2020

(54) RETAINERLESS ORTHODONTIC IMPLANT SYSTEM

(71) Applicant: Todd E. Shatkin, Williamsville, NY (US)

(72) Inventor: Todd E. Shatkin, Williamsville, NY (US)

(*) Notice: Subject to any disclaimer, the term of this patent is extended or adjusted under 35 U.S.C. 154(b) by 300 days.

(21) Appl. No.: 15/698,732

(22) Filed: Sep. 8, 2017

(65) Prior Publication Data

US 2017/0367797 A1 Dec. 28, 2017

Related U.S. Application Data

(63) Continuation of application No. 14/522,668, filed on Oct. 24, 2014, now Pat. No. 9,814,546.

(51) Int. Cl.
| | |
|---|---|
| *A61C 8/00* | (2006.01) |
| *A61C 1/08* | (2006.01) |
| *A61C 7/36* | (2006.01) |
| *A61C 8/02* | (2006.01) |
| *A61F 5/00* | (2006.01) |
| *A61F 5/56* | (2006.01) |

(52) U.S. Cl.
CPC ............ *A61C 8/0096* (2013.01); *A61C 1/084* (2013.01); *A61C 7/36* (2013.01); *A61C 8/0006* (2013.01); *A61C 8/0015* (2013.01); *A61C 8/0016* (2013.01); *A61C 8/0022* (2013.01); *A61C 8/0028* (2013.01); *A61F 5/0006* (2013.01); *A61F 5/566* (2013.01)

(58) Field of Classification Search
CPC ......... A61C 8/0096; A61C 1/084; A61C 7/36; A61C 8/0006; A61C 8/0015; A61C 8/0016; A61C 8/0022; A61C 8/0028; A61F 5/0006; A61F 5/566
See application file for complete search history.

(56) References Cited

U.S. PATENT DOCUMENTS

| | | | |
|---|---|---|---|
| 3,798,773 A | | 3/1974 | Northcutt |
| 4,708,646 A | | 11/1987 | Jasper |
| 5,087,202 A | | 2/1992 | Krenkel |
| 5,183,414 A | | 2/1993 | Czerniawski |
| 5,350,297 A | * | 9/1994 | Cohen ................ A61C 8/00 433/173 |
| 5,775,900 A | * | 7/1998 | Ginsburg ........... A61C 13/0001 433/171 |
| 6,358,052 B1 | | 3/2002 | Lustig et al. |
| 6,416,324 B1 | | 7/2002 | Day |
| 6,719,557 B1 | | 4/2004 | Williams |
| 7,090,490 B2 | | 8/2006 | Graham et al. |

(Continued)

FOREIGN PATENT DOCUMENTS

WO WO2010087824 8/2010

OTHER PUBLICATIONS

The International Search Report (ISR) for International (PCT) Application No. PCT/US2015/055101; dated Jan. 25, 2016.

(Continued)

*Primary Examiner* — Nicholas D Lucchesi
(74) *Attorney, Agent, or Firm* — Phillips Lytle LLP; David L. Principe (57) ABSTRACT

A retainerless orthodontic dental implant system for positioning the mandible forward relative to the maxilla and for facilitating optimal airflow during sleep and a method of using such a system.

13 Claims, 8 Drawing Sheets

(56) References Cited

U.S. PATENT DOCUMENTS

| | | |
|---|---|---|
| 7,108,511 B1 | 9/2006 | Shatkin |
| 7,329,121 B2 | 2/2008 | De Clerck |
| 7,354,270 B2 | 4/2008 | Abolfathi et al. |
| 8,062,032 B2 | 11/2011 | Bulloch et al. |
| 8,640,705 B2 | 2/2014 | Kopp |
| 2002/0137003 A1 | 9/2002 | Knapp |
| 2003/0087217 A1 | 5/2003 | Coatoam |
| 2003/0232308 A1 | 12/2003 | Simmons |
| 2004/0219480 A1 | 11/2004 | Malin |
| 2006/0172251 A1 | 8/2006 | Voudouris |
| 2006/0240378 A1 | 10/2006 | Weinstein et al. |
| 2006/0281046 A1* | 12/2006 | Heo .................. A61C 1/084 433/75 |
| 2007/0259306 A1 | 11/2007 | Raines et al. |
| 2008/0188947 A1* | 8/2008 | Sanders ............ A61B 17/0401 623/23.72 |
| 2009/0032030 A1 | 2/2009 | Callender |
| 2009/0081618 A1* | 3/2009 | Lamar ................. A61C 8/0048 433/218 |
| 2009/0215008 A1 | 8/2009 | Duncan |
| 2010/0297573 A1* | 11/2010 | Yi .......................... A61C 1/084 433/72 |
| 2011/0033820 A1 | 2/2011 | Duncan |
| 2012/0295211 A1 | 11/2012 | Frantz et al. |
| 2013/0138221 A1* | 5/2013 | Junker ................. A61K 31/675 623/23.57 |
| 2014/0011162 A1* | 1/2014 | Zegarelli ............ A61C 13/0013 433/215 |
| 2014/0057222 A1 | 2/2014 | Kumar |
| 2014/0329196 A1* | 11/2014 | Tedesco ................. A61C 1/084 433/34 |
| 2015/0265371 A1* | 9/2015 | Kim ...................... A61C 1/0084 433/214 |
| 2015/0265372 A1* | 9/2015 | Kim .......................... G06T 7/13 433/75 |
| 2016/0184057 A1* | 6/2016 | Shatkin ................ A61C 8/0022 433/75 |

OTHER PUBLICATIONS

The Written Opinion of the searching authority for International (PCT) Application No. PCT/US2015/055101; dated Jan. 25, 2016.

Shingo Kuroda; Akira Katayama; Teruko Takano-Yamamoto; "Severe Anterior Open-Bite Case Treated Using Titanium Screw Anchorage," Angle Orthodontist. vol. 74, No. 4, 2004.

* cited by examiner

FIG. 8 ial airway patency, correcting misalignment of the maxillary incisors, correcting misalignment of the mandibular incisors, and providing a desired occlusal configuration.

RETAINERLESS ORTHODONTIC IMPLANT SYSTEM

CROSS-REFERENCE TO RELATED APPLICATION

The present application claims priority benefit of U.S. Non-provisional patent application Ser. No. 14/522,668 entitled "Retainerless Orthodontic Dental Implant System," which is incorporated herein by reference.

TECHNICAL FIELD

The present invention relates generally to the field of devices for treatment of sleep apnea and related sleep disorders, and more particularly to a retainerless orthodontic dental implant system for positioning the mandible forward relative to the maxilla and a method of using such a system.

BACKGROUND ART

U.S. Pat. No. 8,602,032 discloses an apparatus for maxilla-mandibular fixation.
U.S. Patent Application Publication No. 2009/0032030 discloses an apparatus for treatment of sleep apnea.

BRIEF SUMMARY OF THE INVENTION

With parenthetical reference to the corresponding parts, portions or surfaces of the disclosed embodiment, merely for the purposes of illustration and not by way of limitation, the first aspect of the present invention provides a method of preventing or treating a condition associated with a maxillomandibular aberrancy in a subject, the method comprising (a) providing a guide stent (56) having one or more apertures (68); (b) installing one or more implants (26) in the upper (23) and lower jawbone (20) of the subject such that the one or more implants (26) are substantially aligned with the one or more apertures (68), wherein the one or more implants (26) have at least one orthogonally protruding abutment end (38); (c) removing the guide stent (56); and, (d) providing one or more connectors (41) having a first end (83) configured to attach to the at least one abutment end (38) of the one or more implants (26) in the upper jawbone (23) of the subject, and wherein a second end (86) disposed opposite from the first end (83) is configured to attach to the at least one abutment end (38) of the one or more implants (26) in the lower jawbone (20) of the subject.

In another aspect, the condition is selected from the group consisting of sleep apnea, sleep hypopnea, snoring, temporomandibular joint (TMJ) and muscular disorders, post-operative maxillofacial immobilization, and obesity.

In another aspect, the maxillomandibular aberrancy is selected from the group consisting of mandibular retrusion, post-operative cleft palate surgery, progressive thickening of palatal tissues, retroglossal region obtrusion, tongue position-induced aberrancies, mandibular retrognathia, mandibular retropalatal, lateral pharyngeal wall malformities, retrusive maxilla, impeded nasal aerodynamics, hard palate deformation, alar cartilage deformities or collapse, septal deviations, enlarged turbinates, constriction, and crossbite, and combinations thereof.

In another aspect, the guide stent (56) is composed of a thermoplastic material configured as a topological imprint formed by vacuum imprinting, and wherein the guide stent (56) functions to direct the positioning of the one or more implants (26) through the one or more apertures (68).

In another aspect, the implanting is between apical root regions of the subject's jawbone.

In another aspect, the one or more implants (26) are hollow or solid dental screws, rods, poles, distractors, conduits, members, or tubes. The implants (26) may be installed by means of keys, wrenches, gripping members or the like.

In another aspect, the one or more implants (26) are three right threaded members disposed on the right side of the subject's maxillomandibular midline (44) and three left threaded members disposed on the left side of the subject's maxillomandibular midline (44). Two of the three right threaded members (26) are positioned at the subject's right mandible and one of the three right threaded members (26) is positioned at the subject's right maxillae. Two of the three left threaded members (26) are positioned at the subject's left mandible and one of the three left threaded members (26) is positioned at the subject's left maxillae.

In another aspect, the at least one abutment end (38) remains above the gum-line surface in a buccal orientation after implantation, and wherein the at least one abutment end (38) is capable of engaging with the one or more connectors (41).

In another aspect, the at least one abutment end (38) is capable of receiving one or more of the connectors (41). The connectors (41) are composed of a material selected from the group consisting of injection molded urethane plastic, silicone, rubber, vinyl, non-water hardenable urethane, plastic, plastic-based materials, fiberglass, metal, ceramic, monomers, polymers, terpolymers, resin, plaster, and cellulose.

In another aspect, the one or more connectors (41) possess one or more sizes, lengths, thicknesses, elasticity constants, and wherein the one or more connectors (41) are amenable to personalized modification.

In another aspect, the connectors (41) have openings (83, 86) disposed at the first and second ends (89, 92). The openings (83, 86) may have more than one circumference, and wherein the more than one circumference comprises an interior circumference and a raised interior circumference. The interior circumference and the raised interior circumference are configured at the first and second ends of the connectors (41). The at least one circumference of the opening in the connector reversibly envelopes a terminus of the at least one abutment end (38). The terminus possesses one or more grooves, adherence nodes, or cylindania, to stabilize the engagement.

In another aspect, the one or more implants (26), the one or more apertures (68), the at least one abutment end (38), the one or more connectors (41), or the first and second ends (83, 86) of the connectors (41), have a shape selected from the group consisting of circular, rectangular, coned, pyramidal, grooved, square, polygonal, curved, concentric, concave, convex, perimetric, diamond, hexagonal, and triangular configurations.

In another aspect, the attaching of the connectors (41) to the abutment end (38) is reversible. The attaching may occur through a mechanism selected from the group consisting of snapping, screwing, clamping, adhering, locking, riveting, frictional fitting, and bayonetting.

In another aspect, the one or more implants (26), the one or more apertures (68), the at least one abutment end (38), or the one or more connectors (41) have a surface that is colored, patterned, or textured.

In another aspect, the correcting of the maxillomandibular aberrancy is selected from the group consisting of a mandible shift, maxillary manipulation, retaining the subject's jaw in a desired position, increasing airflow, adjusting upper and/or lower jawbone alignment, adjusting upper and/or lower jawbone proximity with respect to each other, facilitating optimal airflow during sleep, and reversibly fixing the upper jawbone to the lower jawbone.

In another aspect, the mandible shift is a labial shift.

In another aspect, the one or more implants (26) are installed such that each of the one or more implants (26) individually or concertedly possess an orientation relative to the one or more implants within the same or different oral quadrant, and wherein the orientation is selected from the group consisting of lingual, labial, adjacent, buccal, planar, orthogonal, symmetric, asymmetric, tangential, horizontal, perpendicular, rotational, central, lateral, anterior, posterior, above, below, proximal, mesial, opposite, distally, angled, straight, slanted, tapered, diagonal, random, polygonal, rectangular, square, circular, curved, concentric, concave, convex, perimetric, diamond, hexagonal, and triangular configuration.

In another aspect, the one or more implants (26) are designed for transitional dental applications.

In another aspect, the one or more implants (26) are designed for long term dental applications.

In another aspect, the one or more implants (26) are smooth or modified.

In another aspect, the one or more implants (26) are modified by acid etching, decortication and/or blasting.

In another aspect, the one or more implants (26) are modified to include one or more osteoinductive agents, bone graft material, bone substitute material, allograft bone, demineralized bone material, ceramics, coral, collagen and ceramic composite, ossified bone protein, an osteogenesis source, a fusion promoting substance, a bone growth promoting material, bone, bone derived substances, a demineralized bone matrix, a mineralizing protein, a plasma spray coating, an ossifying protein, bone morphogenetic protein, hydroxyapatite, or genes coding for the production of bone.

Another aspect of the invention provides a method of therapeutically adjusting a subject's jaw without using a retainer. The method includes the steps of: (a) installing one or more implants (26) in an upper (23) and lower jawbone (20) of the subject, wherein the one or more implants (26) are orthogonal to the upper (23) and lower jawbone (20) when in an implanted position, and wherein the one or more implants (26) possess at least one buccally oriented abutment end (38); (b) providing one or more bands (41) having a first end (83) and a second end (86) disposed opposite to the first end (83), wherein the first end (83) of the one or more bands (41) is configured to attach to at least one of the abutment ends (38) in a mandibular position when substantially aligned, and wherein the second end (86) of the one or more bands (41) is configured to attach to at least one of the abutment ends (38) in a maxillary position when substantially aligned; (c) substantially aligning the one or more bands (41) with the at least one mandibular abutment end (38) to form a reversibly engaged lower connection; and, (d) substantially aligning the one or more bands (41) with the at least one maxillary abutment end (38) to form a reversibly engaged upper connection, wherein the engaged upper connection in conjunction with the engaged lower connection imparts tension to the one or more bands (41), and wherein the tension functions to therapeutically adjust the subject's jaw without the use of a retainer.

In another aspect, the therapeutic adjustment is indicated for preventing or treating a condition selected from the group consisting of sleep apnea, sleep hypopnea, snoring, temporomandibular joint (TMJ) and muscular disorders, post-operative oral-maxillofacial immobilization, and obesity.

In another aspect, the subject is afflicted with one or more physiological conditions selected from the group consisting of mandibular retrusion, post-operative cleft palate surgery, progressive thickening of palatal tissues, retroglossal region obtrusion, tongue position-induced aberrancies, mandibular retrognathia, mandibular retropalatal, lateral pharyngeal wall malformities, retrusive maxilla, impeded nasal aerodynamics, hard palate deformation, alar cartilage deformities or collapse, septal deviations, enlarged turbinates, constriction, and crossbite.

In another aspect, the implanting is between apical root regions of the upper and lower jawbone.

In another aspect, the one or more implants (26) are at least six total threaded members implanted in the subject's mandible and maxilla in an orientation selected from the group consisting of lingual, labial, adjacent, buccal, planar, orthogonal, symmetric, asymmetric, tangential, horizontal, perpendicular, rotational, central, lateral, anterior, posterior, above, below, proximal, mesial, opposite, distally, angled, straight, slanted, tapered, diagonal, random, polygonal, rectangular, square, circular, curved, concentric, concave, convex, perimetric, diamond, hexagonal, and triangular configuration.

In another aspect, the at least one abutment end (38) remains above the gum-line surface in a buccal orientation after implantation, and wherein the at least one abutment end (38) is capable of securing to the one or more bands.

In another aspect, the at least one abutment end is capable of receiving and securing to multiple combinations of the one or more of the bands (41).

In another aspect, the bands are composed of materials selected from the group consisting of injection molded urethane plastic, silicone, rubber, vinyl, non-water hardenable urethane, plastic, plastic-based materials, fiberglass, metal, ceramic, monomers, polymers, terpolymers, resin, plaster, and cellulose.

In another aspect, the one or more bands (41) possess one or more sizes, lengths, thicknesses, elasticity constants.

In another aspect, the first (83) and second ends (86) of the one or more bands (41) have openings (89, 92) that are configured as multilevel conduits for circumferentially connecting to a terminal region of the at least one abutment end (38). The circumferential connecting provides for a rotatable interaction.

In another aspect, the one or more implants (26), the at least one abutment end (38), the one or more bands (41) have a shape selected from the group consisting of circular, rectangular, coned, pyramidal, grooved, square, polygonal, curved, concentric, concave, convex, perimetric, diamond, hexagonal, and triangular configuration.

In another aspect, the one or more implants (26), the at least one abutment end (38), the one or more bands (41) have a surface, and wherein the surface is colored, patterned, or textured.

In another aspect, the substantial alignment provides for the reversibly engaged lower connection and the reversibly engaged upper connection by an interaction selected from the group consisting of snapping, screwing, clamping, adhering, locking, riveting, frictional fitting, and bayonetting.

In another aspect, the therapeutic adjustment is a mandible shift, maxillary manipulation, retaining the subject's jaw in a desired position, increasing airflow, adjusting upper and/or lower jawbone alignment, adjusting upper and/or lower jawbone proximity with respect to each other, facilitating optimal airflow during sleep, and reversibly fixing the upper jawbone to the lower jawbone. The mandible shift may be a labial shift.

In another aspect, the one or more implants (26) are implanted such that each of the one or more implants (26) individually or concertedly possess an orientation relative to the one or more implants (26) within the same or different oral quadrant, and wherein the orientation is selected from the group consisting of lingual, labial, adjacent, buccal, planar, orthogonal, symmetric, asymmetric, tangential, horizontal, perpendicular, rotational, central, lateral, anterior, posterior, above, below, proximal, mesial, opposite, distally, angled, straight, slanted, tapered, diagonal, random, polygonal, rectangular, square, circular, curved, concentric, concave, convex, perimetric, diamond, hexagonal, and triangular configuration.

In another aspect, the one or more implants (26) are designed for transitional dental applications.

In another aspect, the one or more implants (26) are designed for long term dental applications.

In another aspect, the one or more implants (26) are smooth or modified. The one or more implants (26) may be modified by acid etching, decortication and/or blasting.

Another aspect of the invention may comprise an apparatus for treating or preventing a maxillomandibular condition. The apparatus includes (a) a guide stent (56) having one or more apertures (68); (b) one or more implants (26), wherein each of the one or more implants (26) have a tip (32) and an abutment end (38) connected by a body (27); (c) one or more bands (41); and (d) a securing mechanism that reversibly connects the one or more implants to the one or more bands.

In another aspect, the guide stent (56) is composed of a thermoplastic material configured as a topological imprint formed by vacuum imprinting, and wherein the guide stent (56) functions to direct the positioning of the one or more implants (26) through the one or more apertures (68).

In another aspect, the tip (32) of the one or more implants (26) is disposed between apical root regions of a subject's jaw.

In another aspect, the implant (26) is a partially implanted anchor.

In another aspect, the abutment end (38) remains above the gum-line surface in a buccal orientation after implantation.

In another aspect, the abutment end (38) is capable of receiving one or more of the bands (41).

In another aspect, the bands (41) are composed of a material selected from the group consisting of injection molded urethane plastic, silicone, rubber, vinyl, non-water hardenable urethane, plastic, plastic-based materials, fiberglass, metal, ceramic, monomers, polymers, terpolymers, resin, plaster, and cellulose.

In another aspect, the bands (41) possess one or more sizes, lengths, thicknesses, and elasticity constants.

In another aspect, the securing mechanism is selected from the group consisting of one or more snapping components, screws, clamps, adhesives, rivets, locks, and friction fitting components.

Another aspect of the invention provides a system for treating or preventing an orofacial condition. The system may comprise (a) a guide stent (56) having one or more apertures (68), wherein the guide stent (56) is composed of a thermoplastic material configured as a topological imprint formed by vacuum imprinting; (b) one or more implants (26) for installation between apical root regions of a subject's jaw such that the one or more implants (26) are substantially aligned with the one or more apertures (68), wherein the one or more implants (26) have a tip (32) and an abutment end (38) connected by a body (27); (c) one or more pliable bands (41) having a first end (83) and a second end (86), wherein the one or more pliable bands (41) induce movement of the subject's jaw when in an engaged configuration; and (d) an engagement mechanism to induce the engage configuration and alleviate or prevent the orofacial condition.

In another aspect of the invention, the guide stent (56) functions to direct the positioning of the one or more implants (26) through the one or more apertures (68).

In another aspect of the invention, the implant (26) is a partially implanted anchor.

In another aspect of the invention, the abutment end (38) remains above the gum-line surface in a buccal orientation after implantation.

In another aspect of the invention, the one or more implants (26) are installed in all four maxillomandibular quadrant regions of the subject.

In another aspect of the invention, the abutment end (38) is capable of receiving multiple configurations of the one or more pliable bands (41). The pliable bands (41) may be comprised of a material selected from the group consisting of injection molded urethane plastic, silicone, rubber, vinyl, non-water hardenable urethane, plastic, plastic-based materials, fiberglass, metal, ceramic, monomers, polymers, terpolymers, resin, plaster, and cellulose. The pliable bands (41) may possess one or more sizes, lengths, thicknesses, and elasticity constants.

In another aspect of the invention, the engagement mechanism is selected from the group consisting of one or more snapping components, screws, clamps, adhesives, rivets, locks, and friction fitting components.

In another aspect of the invention, the system can be used as a weight management tool for obesity by restricting mouth opening during the day as obesity and sleep disorders go hand in hand in many cases.

DESCRIPTION OF THE EMBODIMENTS

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Figure 1:
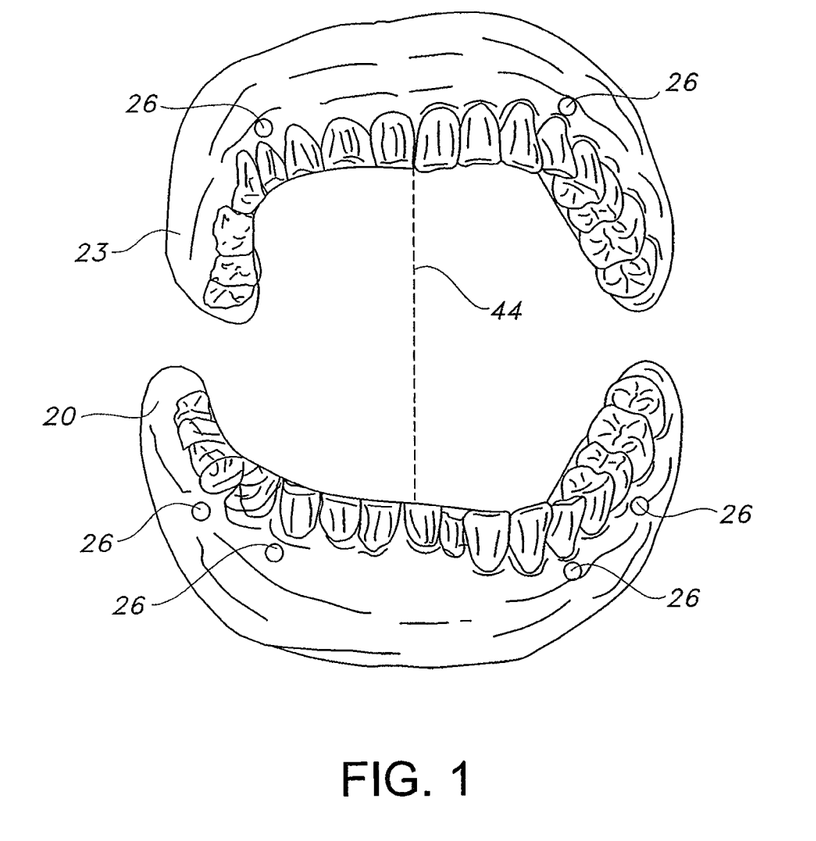
FIG. 1 is a front view of both upper and lower jaws of a human mouth containing implants of the present invention.
Figures 2A, 2B, 2C:
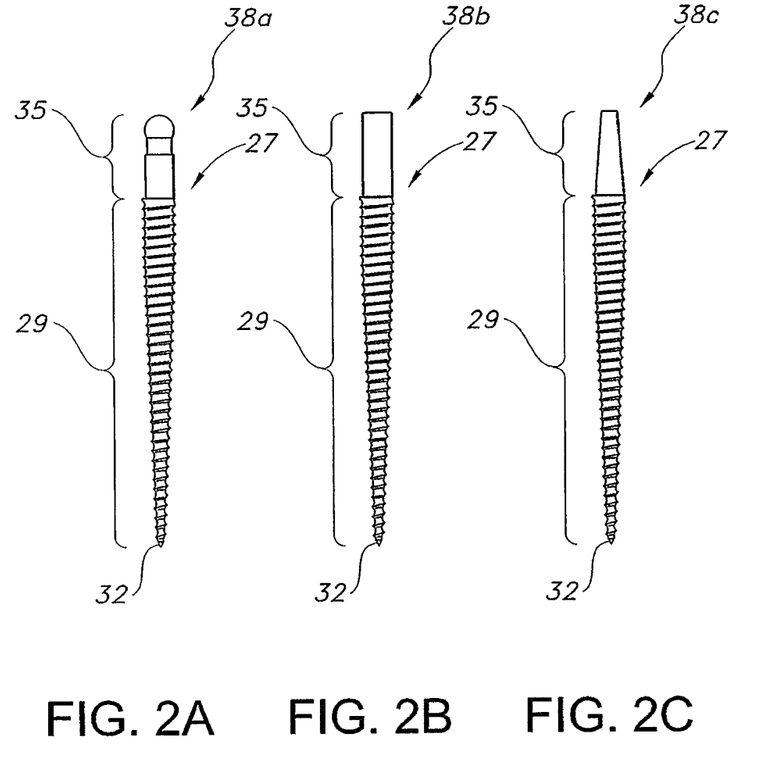
FIGS. 2A-2C are front elevational views of various embodiments of the implant.

Referring to the drawings, FIG. 1 is a front view of lower jaw 20 and upper jaw 23 each supporting implants 26. Implants 26 are inserted into the bone material of lower jaw 20 and upper jaw 23. The implants 26 may comprise threaded members. The threaded members may include hollow or solid dental screws, rods, poles, distractors, conduits, members, tubes, keys, wrenches, or gripping members. The implants 26 may also comprise threaded anchors. FIGS. 2A-2C are views of several embodiments of implant 26. Implant 26 includes a body 27 ranging in diameter from 1.6 to 2.5 mm. Different diameters may be selected depending on the density of the bone material that will support implant 26. Threaded section 29 extends from tip 32 to carrier section 35. Tip 32 has a point sufficient to enable implant 26 to be self-tapping when it is inserted into lower jawbone 20 or upper jawbone 23. Carrier section 35 is configured in such a way as to allow instruments such as suitably sized wrenches, ratchets or similar tools to grab and turn implant 26 in order to screw implant 26 into bone material. Abutment end 38 is at the opposite end of implant 26 from tip 32. Abutment end 38 may have any shape including a spherical abutment end 38a, a square or rectangular solid abutment end 38b, or a polygonal tapered end, such as a pyramidal shaped abutment end 38c. Other embodiments of abutment end 38 may include any shape suitable for attaching to a connector 41 as described herein.

Returning to FIG. 1, the implants 26 may be positioned between apical root regions of the subject's jawbone. The implants 26 may include three right threaded members disposed on the right side of the subject's maxillomandibular midline 44 and three left threaded members on the left side of the subject's maxillomandibular midline 44. Two of the three right threaded members may be positioned at the subject's right lower jaw 20 and one of the three right threaded members may be positioned at the subject's right upper jaw 23. Two of the three left threaded members may be positioned at the subject's left lower jaw 20 and one of the three left threaded members may be positioned at the subject's left upper jaw 23. After implantation, the abutment end 38 of the implant 26 remains above the gum-line surface in a buccal orientation.

The implants 26 may be disposed orthogonal to the lower and upper jawbones 20, 23 when implanted. The implants 26 may be modified to include one or more materials such as osteoinductive agents, bone graft material, bone substitute material, allograft bone, demineralized bone material, ceramics, coral, collagen and ceramic composite, ossified bone protein, an osteogenesis source, a fusion promoting substance, a bone growth promoting material, bone, bone derived substances, a demineralized bone matrix, a mineralizing protein, hydroxyapatite, or genes coding for the production of bone.

Figure 3:
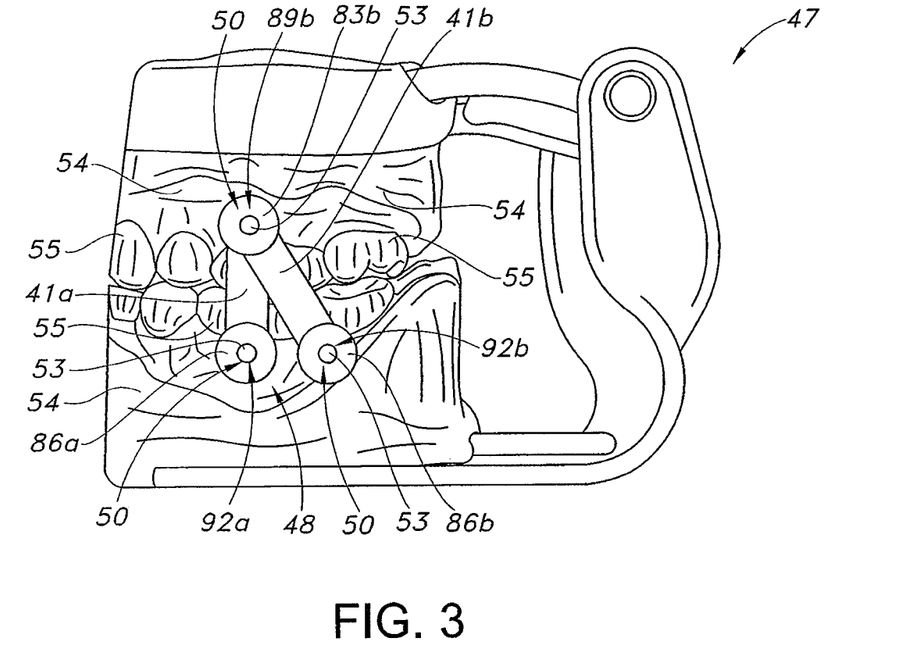
FIG. 3 is a side elevational view of a model showing one example of positioning for the implants and connectors.

FIG. 3 depicts a model 47 created from an impression made of the lower and upper jaws 20, 23 of the subject. The fabrication of such a model 47 is well known to those skilled in the art. The model 47 provides for determining the positioning of the implants 26 and the positioning and length of the connectors 41. The connectors 41 are used to adjust the mandible shift, maxillary manipulation, to retain the subject's jaw in a desired position, to increase airflow, to adjust upper and/or lower jawbone alignment, to adjust upper and/or lower jawbone proximity with respect to each other, to facilitate optimal airflow during sleep, or to reversibly fix the upper jawbone to the lower jawbone. The mandible shift may be a labial shift.

Implant orifices or holes 50 are drilled or bored into the model 47 and implant analogs 53 are placed into the holes. Implant analogs 53 have abutment ends and carrier sections similar in size to actual implants 26 but they may lack threaded sections because there is no need to tap into model 47. A guide stent 56 (FIG. 4) is made from any suitable thermoplastic material capable of vacuum forming over the model 47. The vacuum process molds the stent material into the shape of the implant receiving area 48 comprising the implant analogs 53, the gums 54, and the surrounding teeth 55. In one example of the stent forming procedure, cylinders 62 (FIG. 4) may be placed around implant analogs 53 and into the holes 50 so that the cylindrical wall 59 of the cylinders 62 surrounds the body of implant analogs 53 with the abutment end 65 of the implant analog 53 remaining uncovered. With cylinders 62 in place, the vacuum forming process incorporates the cylinders 62 into the molded guide stent 56 creating guide holes 68 as part of the molded guide stent 56.

Figure 4:
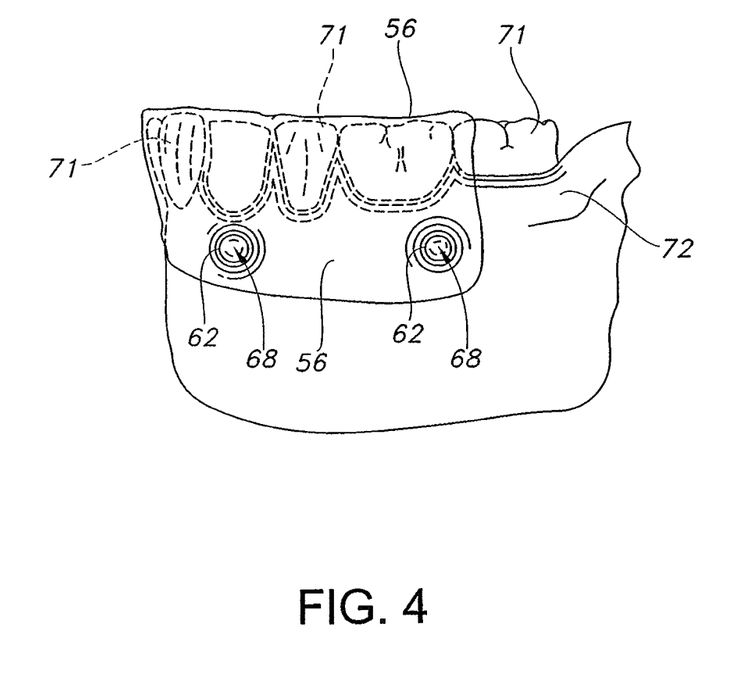
FIG. 4 is an elevational side view showing a guide molding stent positioned over the lower jaw of a subject.

FIG. 4 is a side elevational view showing the guide stent 56 with incorporated guide holes 68 which is molded to the shape of the area of a patient's jaw where implants 26 are to be placed. To insert implants 26 into lower jaw 20 or upper jaw 23, the molded guide stent 56 is placed over the teeth 71 where the implants 26 are to be placed. As a result of the vacuum forming process described above, the configuration of the molded guide stent 56 enables it to fit or overlay snugly on the teeth 71 and gums 72 of the subject and the guide holes 68 are positioned at the predetermined locations analogous to the positions of implant analogs 53 in the model 47. Moreover, the incorporation of cylinders 62 into the molded guide stent 56 orients the guide holes 68 orthogonal to the jaw for inserting implants 26 into the bone material.

Figure 5:
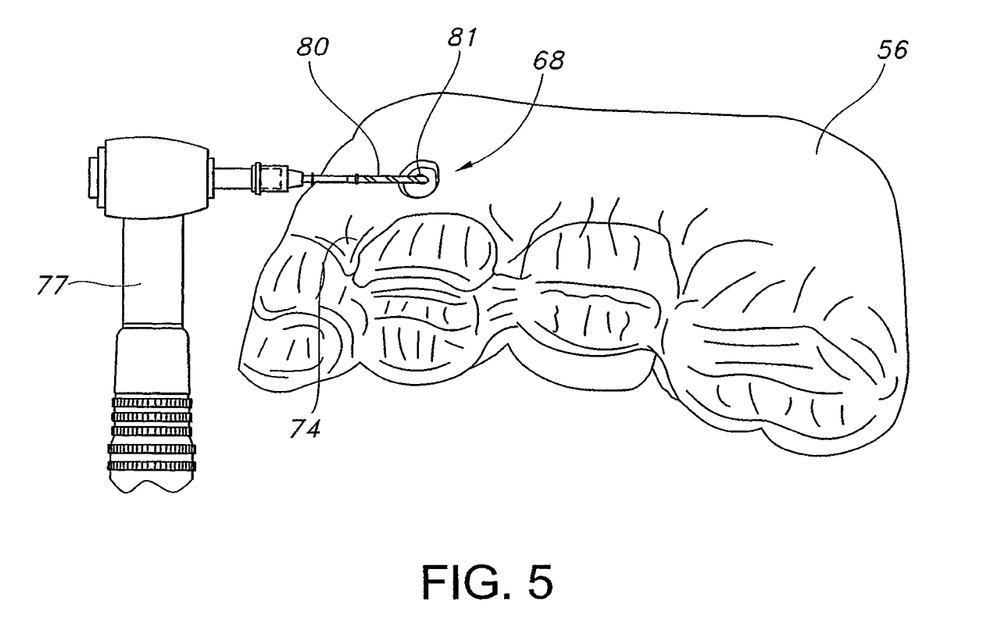
FIG. 5 is a perspective view showing the preparation for placement of the implant in an upper jaw.

FIG. 5 is a perspective view of a guide stent 56 for use on the upper jaw 23 depicting the preparation for inserting implant 26 into bone material above the gum line 74. After using a local anesthetic to desensitize the area, drill 77 with drill bit 80 is used to prepare a starter hole 81 by positioning drill bit 80 through the guide hole 68 and drilling through the gum and about 4-8 mm into the underlying bone. By drilling through guide hole 68, the operator and patient are assured that the starter hole 81 is placed at the desired location and is drilled at the desired angle to ensure, as much as possible, that the starter hole 81 is surrounded by bone material of equal mass. Drill bit 80 has a smaller diameter than that of implant 26. After preparing the starter holes 81, implant(s) 26 are threaded or screwed into the starter holes 81 until only a portion of the body 27 and the abutment end 38 are protruding from the gums 72 of the subject. Wrenches, ratchets and similar tools may be used to screw implants 26 into the bone material.

Figure 8:
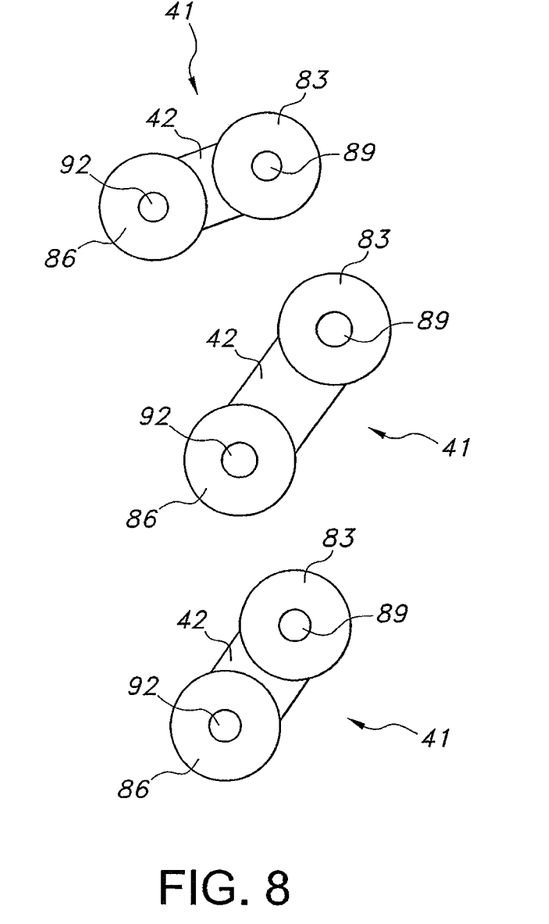
FIG. 8 is a top plan view of one example of the connectors.

Returning to FIG. 3, once the implants 26 are installed at their predetermined locations, connectors 41 may be attached to the implants. The connectors 41a, 41b may have a first end 83a, 83b disposed opposite from a second end 86a, 86b. The first and second ends 83, 86 may have first and second openings 89, 92 for securing to the abutment ends 38 of the implants 26. The connectors 41 (best shown in FIG. 8) may be composed of a material selected from the group consisting of injection molded urethane plastic, silicone, rubber, vinyl, non-water hardenable urethane, plastic, plastic-based materials, fiberglass, metal, ceramic, monomers, polymers, terpolymers, resin, plaster, and cellulose. The connectors 41 may be custom designed to have different sizes, lengths, thicknesses, elasticity constants or the like depending on the application and the size of the patient's jaw. For example, as shown in FIG. 8, the length of the connectors 41 may be varied by varying the length of the midportion 42. Turning to FIG. 3 a first connector 41*a* is disposed vertically between an implant analog 53 on the upper jaw 23 and an implant analog 53 on the lower jaw 20. Connector 41*a* may be used to adjust the air flow path to provide optimal air flow during sleep. A different connector 41*a* may also be used as a weight management tool by restricting mouth opening during the day.

Connector 41*b* is disposed diagonally between an implant analog 53 on the upper jaw 23 and an implant analog 53 on the lower jaw 20. The size and elasticity of connector 41*b* may be adjusted to provide adjustment of the alignment between the upper and lower jaw of the subject for treatment of conditions such as sleep apnea, sleep hypopnea, snoring, and temporomandibular joint (TMJ) and muscular disorders. The combined effect of connectors 41*a* and 41*b* may also be used to treat these conditions.

When the system is installed, the attachment of the connectors 41*a*, 41*b* to the abutment end 38 of the implant 26 is reversible. The attaching may occur through various mechanisms, including but not limited to, snapping, screwing, clamping, adhering, locking, riveting, frictional fitting and bayonetting. In the example shown, the attaching is accomplished by inserting the connector 41 such that the abutment ends 38 of two implants 26 are received in the opposed openings 89, 92 located on the connector 41. Other means of attaching the connectors 41 may also be evident to those of ordinary skill in the art based on this disclosure.

Figure 6:
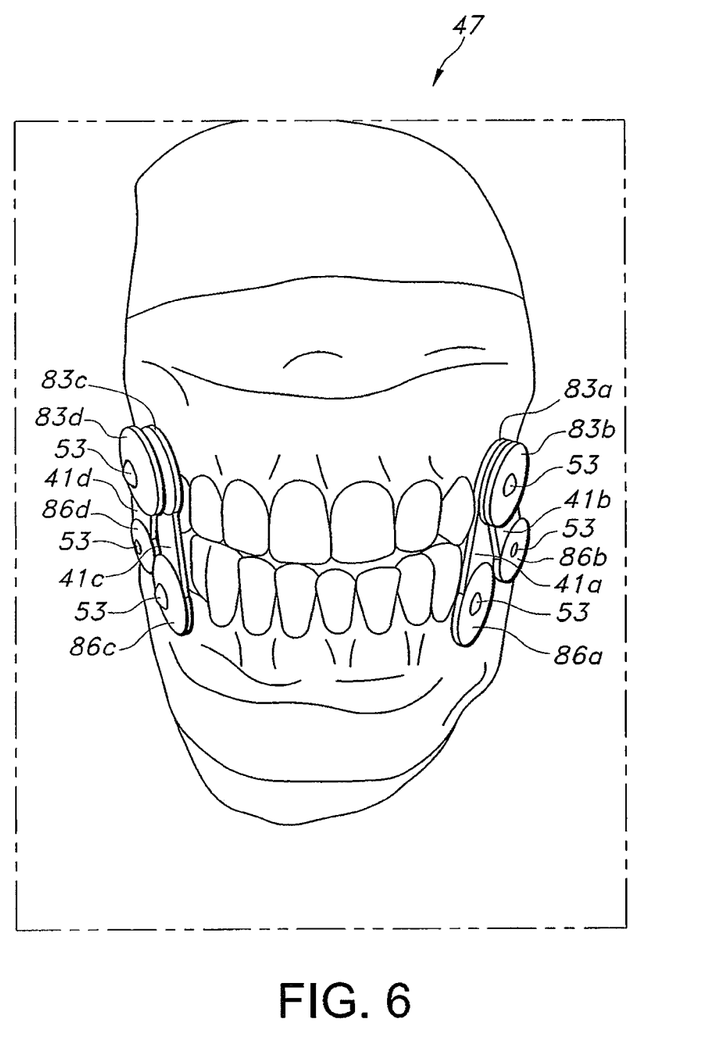
FIG. 6 is a front perspective view of a model showing the implant analogs and connectors.
Figure 7:
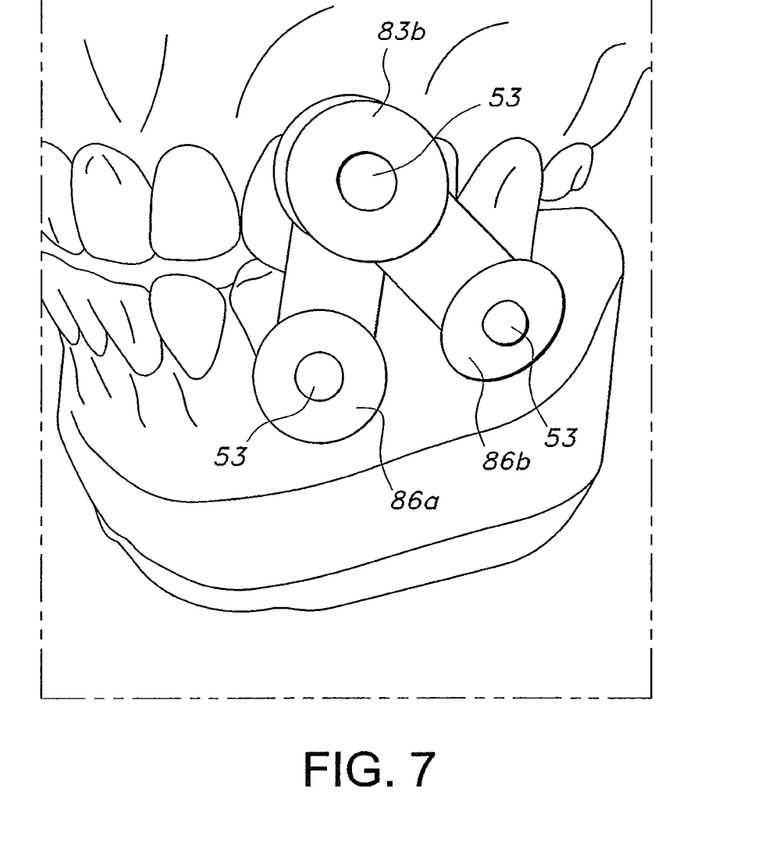
FIG. 7 is a side perspective view of the model shown in FIG. 6.

Turning to FIGS. 6-7, the model 47 is shown with connectors 41*a*, 41*b*, 41*c*, and 41*d* attached between implant analogs 53 disposed on the left and right hand sides of the upper and lower jaws.

The present invention contemplates that many changes and modifications may be made. Therefore, while the presently-preferred form of the retainerless orthodontic implant system has been shown and described, and several modifications and alternatives discussed, persons skilled in this art will readily appreciate that various additional changes and modifications may be made without departing from the spirit of the invention, as defined and differentiated by the following claims.

What is claimed is:

1. A method of preventing or treating a condition associated with a maxillomandibular aberrancy in a subject, the method comprising:
    (a) providing a guide stent having one or more apertures;
    (b) installing one or more implants in the upper and lower jawbone of the subject such that the one or more implants are substantially aligned with the one or more apertures, wherein the one or more implants have at least one orthogonally protruding abutment end;
    (c) removing the guide stent; and,
    (d) providing one or more connectors having a first end configured to attach to the at least one abutment end of the one or more implants in the upper jawbone of the subject, and wherein a second end disposed opposite from the first end is configured to attach to the at least one abutment end of the one or more implants in the lower jawbone of the subject.

2. The method of claim 1, wherein the guide stent is composed of a thermoplastic material configured as a topological imprint formed by vacuum imprinting, and wherein the guide stent functions to direct the positioning of one or more threaded members through the one or more apertures.

3. The method of claim 1, wherein the one or more implants are installed between apical root regions of the subject's jawbone.

4. The method of claim 1, wherein the one or more implants are three right threaded members disposed on the right side of the subject's maxillomandibular midline and three left threaded members disposed on the left side of the subject's maxillomandibular midline.

5. The method of claim 4, wherein two of the three right threaded members are positioned at the subject's right mandible and one of the three right threaded members is positioned at the subject's right maxillae, and wherein two of the three left threaded members are positioned at the subject's left mandible and one of the three left threaded members is positioned at the subject's left maxillae.

6. The method of claim 1, wherein the at least one abutment end remains above the gum-line surface in a buccal orientation after implantation.

7. The method of claim 1, wherein the one or more connectors are composed of a material selected from the group consisting of injection molded urethane plastic, silicone, rubber, vinyl, non-water hardenable urethane, plastic, plastic-based materials, fiberglass, metal, ceramic, monomers, polymers, terpolymers, resin, plaster, and cellulose.

8. The method of claim 1, wherein the one or more connectors have openings disposed at the first and second ends.

9. The method of claim 1, wherein attaching the one or more connectors occurs through a mechanism selected from the group consisting of snapping, screwing, clamping, adhering, locking, riveting, frictional fitting, and bayonetting.

10. The method of claim 1, wherein the one or more implants comprise a threaded section.

11. The method of claim 1, wherein the one or more implants are modified by acid etching, decortication and/or blasting.

12. The method of claim 1, wherein the one or more implants are modified to include one or more osteoinductive agents, bone graft material, bone substitute material, allograft bone, demineralized bone material, ceramics, coral, collagen and ceramic composite, ossified bone protein, an osteogenesis source, a fusion promoting substance, a bone growth promoting material, bone, bone derived substances, a demineralized bone matrix, a mineralizing protein, a plasma spray coating, an ossifying protein, bone morphogenetic protein, hydroxyapatite, or genes coding for the production of bone.

13. An apparatus for treating or preventing a maxillomandibular condition in a subject, the apparatus comprising:
    (a) a guide stent having one or more apertures;
    (b) one or more implants for installation between apical root regions of the subject's jaw such that the one or more implants are substantially aligned with the one or more apertures, wherein each of the one or more implants has a tip and an abutment end connected by a body;

(c) one or more bands, wherein the one or more bands induce movement of the subject's jaw when in an engaged configuration; and
(d) a securing mechanism that reversibly connects the one or more implants to the one or more bands.

* * * * *